(12) United States Patent
LaBarbera et al.

(10) Patent No.: US 11,756,683 B2
(45) Date of Patent: *Sep. 12, 2023

(54) PATIENT DATA COLLECTION SYSTEM AND METHOD

(71) Applicant: Midmark Corporation, Versailles, OH (US)

(72) Inventors: Bradley J. LaBarbera, Troy, OH (US); Thomas D. Schwieterman, Cincinnati, OH (US)

(73) Assignee: Midmark Corporation, Versailles, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/982,986

(22) Filed: Nov. 8, 2022

(65) Prior Publication Data

US 2023/0060448 A1 Mar. 2, 2023

Related U.S. Application Data

(63) Continuation of application No. 17/094,354, filed on Nov. 10, 2020, now Pat. No. 11,508,478.

(60) Provisional application No. 62/933,551, filed on Nov. 11, 2019.

(51) Int. Cl.
*G16H 40/67* (2018.01)
*G16H 40/20* (2018.01)
*A61B 5/00* (2006.01)
*A61B 5/024* (2006.01)
*G16H 10/60* (2018.01)

(52) U.S. Cl.
CPC ......... *G16H 40/67* (2018.01); *A61B 5/02438* (2013.01); *A61B 5/681* (2013.01); *G16H 10/60* (2018.01); *G16H 40/20* (2018.01)

(58) Field of Classification Search
None
See application file for complete search history.

(56) References Cited

U.S. PATENT DOCUMENTS

| 6,154,139 | A | 11/2000 | Heller |
| 6,838,992 | B2 | 1/2005 | Tenarvitz |
| 11,508,478 | B2 | 11/2022 | LaBarbera et al. |
| 2017/0143566 | A1 | 5/2017 | Elku et al. |
| 2018/0168463 | A1* | 6/2018 | Morris ................. A61B 5/0031 |

* cited by examiner

*Primary Examiner* — Joseph D Burgess
(74) *Attorney, Agent, or Firm* — Frost Brown Todd LLP

(57) ABSTRACT

Various systems and methods for collecting patient data are discussed herein. According to some systems and methods, a timer may be started, and a blood pressure data collection system is actuated to obtain a blood pressure measurement of a patient upon the expiration of the timer. The timer may be incorporated into a patient data collection system or method to ensure the patient is relaxed and calm prior to taking a blood pressure measurement. An event may be sensed by an environmental sensor system and the timer may be started in response to sensing the event. A clinician leaving a room where the patient is disposed is one example of an event. An interruption may be sensed by the environmental sensor system and the timer may be terminated in response to sensing the interruption. The clinician entering the room where the patient is disposed in one example of an interruption.

9 Claims, 6 Drawing Sheets

PATIENT DATA COLLECTION SYSTEM AND METHOD

PRIORITY

This application claims the benefit of U.S. Provisional App. No. 62/933,551 entitled "Patient Data Collection System and Method," filed Nov. 11, 2019, the disclosure of which is incorporated by reference herein.

BACKGROUND

Inaccurate patient data such as blood pressure measurement readings may be caused by common environmental or interpersonal interactions between a patient and a healthcare facility and/or a clinician. For example, a patient sitting down in an unfamiliar room with an unknown clinician standing beside taking a blood pressure reading will often skew the result of the reading. Thus, there is a need in the art for reducing the environmental and interpersonal stressors before obtaining a blood pressure measurement for a patient.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
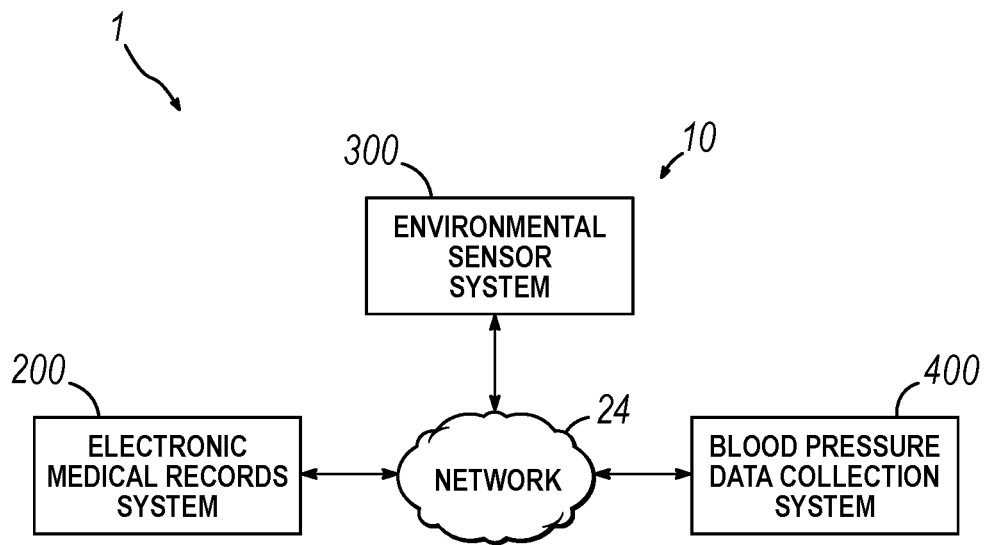
FIG. 1 depicts a diagrammatic view of an exemplary patient data collection system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY PATIENT DATA COLLECTION SYSTEM

Referring now to FIG. 1, a patent data collection system (1) of the present invention may include an operating environment (10). In general, patient data collection system (1) operates to coordinate and broker various issues or situations that arise regarding collecting patient data such as a patient's blood pressure measurement or other patient data, and in particular between a patient, a clinician, and an electronic medical records system, such as an electronic medical records (EMR) system (200). As used herein, a clinician is intended to include the person(s) performing the test, such as a doctor, nurse, nurse practitioner, caregiver, etc. Patient data collection system (1) may further include an environmental sensor system (300) and a blood pressure data collection system (400) within exemplary operating environment (10).

In some versions of operating environment (10), EMR system (200), environmental sensor system (300), and blood pressure data collection system (400) may send and receive communications between one another directly. Alternatively, in other versions of operating environment (10), EMR system (200), environmental sensor system (300), and blood pressure data collection system (400) may communicate with each other indirectly through a network (24). Network (24) may include one or more private and/or public networks (e.g. the Internet) that enable the exchange of data.

One of the features of patient data collection system (1) is related to taking an accurate blood pressure measurement of a patient. In some environments, a patient who has rested for a number of minutes in a generally static position may provide a more accurate blood pressure measurement. Similarly, those patients who have refrained from conversing, interacting, or even seeing a clinician may provide a more accurate blood pressure measurement. Still further, those patients who are situated in a preferred body position with back and feet support as well as their arm supported at heart level with legs uncrossed may provide a more accurate blood pressure measurement. Patient data collection system (1) is configured to address the positioning and interaction issues related to taking an accurate blood pressure measurement of the patient.

i. Exemplary Computer System

Figure 2:
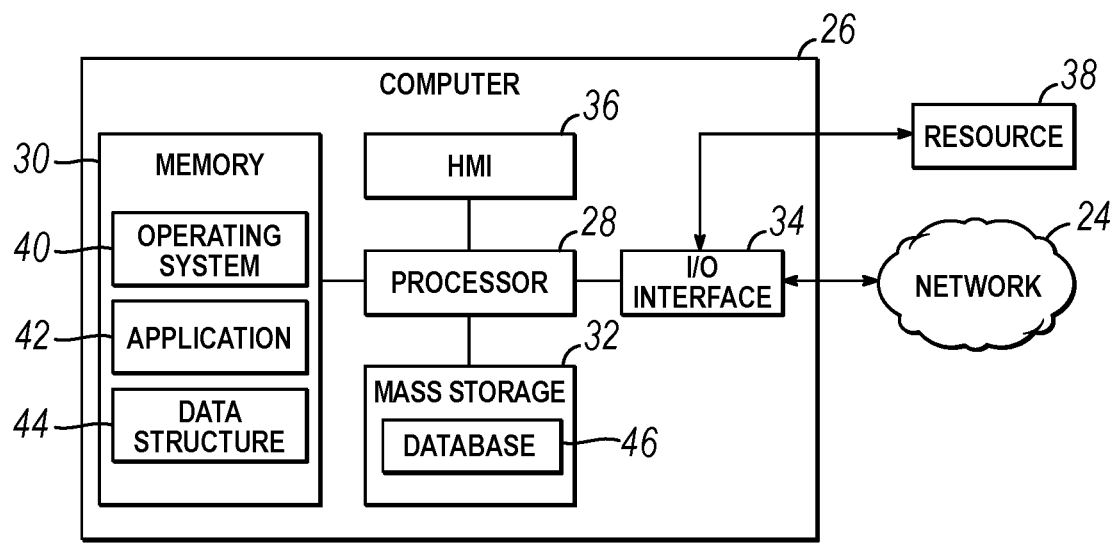
FIG. 2 depicts a diagrammatic view of an exemplary computer system of the patient data collection system of FIG. 1.

Referring now to FIG. 2, EMR system (200), environmental sensor system (300), blood pressure data collection system (400), and network (24) of operating environment (10) may be implemented on one or more computing devices or systems, such as an exemplary computer system (26). Computer system (26) may include a processor (28), a memory (30), a mass storage memory device (32), an input/output (I/O) interface (34), and a Human Machine Interface (HMI) (36). Computer system (26) may also be operatively coupled to one or more external resources (38) via network (24) or I/O interface (34). External resources may include, but are not limited to, servers, databases, mass storage devices, peripheral devices, cloud-based network services, or any other suitable computer resource that may used by computer system (26).

Processor (28) may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in memory (30). Memory (30) may include a single memory device or a plurality of memory devices including, but not limited, to read-only memory (ROM), random access memory (RAM), volatile memory, non-volatile memory, static random access memory (SRAM), dynamic random access memory (DRAM), flash memory, cache memory, or any other device capable of storing information. Mass storage memory device (32) may include data storage devices such as a hard drive, optical drive, tape drive, non-volatile solid state device, or any other device capable of storing information.

Processor (28) may operate under the control of an operating system (40) that resides in memory (30). Operating system (40) may manage computer resources so that computer program code embodied as one or more computer software applications, such as an application (42) residing in memory (30), may have instructions executed by processor (28). In an alternative embodiment, processor (28) may execute the application (42) directly, in which case operating system (40) may be omitted. One or more data structures (44) may also reside in memory (30), and may be used by processor (28), operating system (40), or application (42) to store or manipulate data.

I/O interface (34) may provide a machine interface that operatively couples processor (28) to other devices and systems, such as network (24) or external resource (38). Application (42) may thereby work cooperatively with network (24) or external resource (38) by communicating via I/O interface (34) to provide the various features, functions, applications, processes, or modules comprising embodiments of the invention. Application (42) may also have program code that is executed by one or more external resources (38), or otherwise rely on functions or signals provided by other system or network components external to computer system (26). Indeed, given the nearly endless hardware and software configurations possible, persons having ordinary skill in the art will understand that embodiments of the invention may include applications that are located externally to computer system (26), distributed among multiple computers or other external resources (38), or provided by computing resources (hardware and software) that are provided as a service over network (24), such as a cloud computing service.

HMI (36) may be operatively coupled to processor (28) of computer system (26) in a known manner to allow a user to interact directly with computer system (26). HMI (36) may include video or alphanumeric displays, a touch screen, a speaker, and any other suitable audio and visual indicators capable of providing data to the user. HMI (36) may also include input devices and controls such as an alphanumeric keyboard, a pointing device, keypads, pushbuttons, control knobs, microphones, etc., capable of accepting commands or input from the user and transmitting the entered input to processor (28).

A database (46) may reside on mass storage memory device (32), and may be used to collect and organize data used by the various systems and modules described herein. Database (46) may include data and supporting data structures that store and organize the data. In particular, database (46) may be arranged with any database organization or structure including, but not limited to, a relational database, a hierarchical database, a network database, or combinations thereof. A database management system in the form of a computer software application executing as instructions on processor (28) may be used to access the information or data stored in records of database (46) in response to a query, where a query may be dynamically determined and executed by operating system (40), other applications (42), or one or more modules.

ii. Exemplary Electronic Medical Records System

Figure 3:
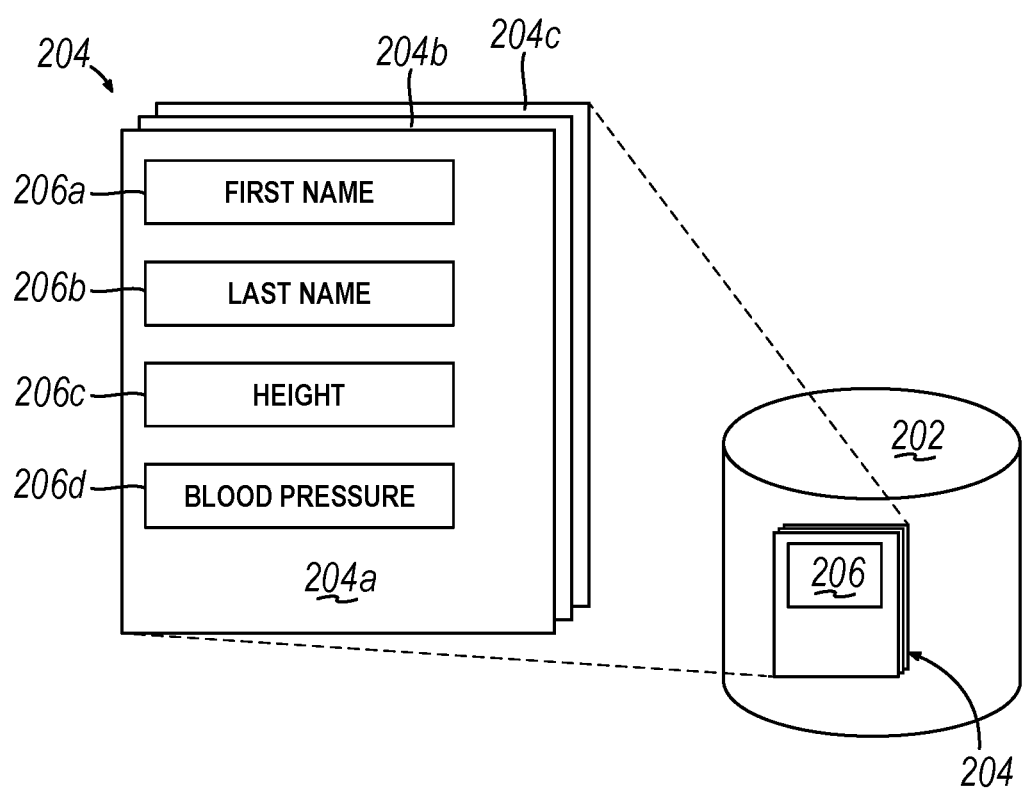
FIG. 3 depicts a diagrammatic view of an exemplary database system of the patient data collection system of FIG. 1.

As shown in FIG. 3, in some versions of patient data collection system (1), database (46) may comprise a medical records database (202) associated with EMR system (200). Medical records database (202) contains a set of medical records (204), with at least one record associated with a patient and containing patient data in at least one data field (206). For example, as shown in FIG. 3 with medical record (204a), field (206a) may contain a patient's first name, field (206b) may contain the patient's last name, field (206c) may contain a patient's height or weight, and field (206d) may contain a patient's current blood pressure reading. The information in the at least one data field (206) may be updated and stored within medical records database (202) for use by EMR system (200) as needed or desired by patient data collection system (1). Medical records (204a, 204b) may contain the same, similar, or different fields compared to fields (206a-206d). For example, medical record (204b, 204c) may contain information pertaining to different patients compared to medical record (204a).

In addition, or in the alternative, other metrics or data regarding the patient, physician, medical environment, or the like may be stored in database (46) or otherwise available through patient data collection system (1). In some versions of medical records (204), environmental adjustments regarding the patient's positioning or other environmental variables may be stored in the patient's medical record (204). For example, the patients preferred examination table height may be stored in the patient's medical record (204). Alternatively, the physician's preferred examination table height for a particular patient may be stored in the patient's medical record (204).

iii. Exemplary Environmental Sensor System

Exemplary environmental sensor system (300) is configured to track at least one person, as the person moves about the healthcare environment. In some versions of environmental sensor system (300), the person may be a patient (302) within the healthcare environment. In other versions, the person may be a clinician (304) within the healthcare environment. In other versions, environmental sensor system (300) is configured to track both patient (302) and clinician (304) within the healthcare environment.

As used herein, the healthcare environment is intended to include a hospital, a physician office having one or more physicians, a skilled nursing facility (e.g. a short term care facility or a long term care facility), or another healthcare setting. For example, as shown in FIG. 4, patient (302) may be associated with a sensor (308) of environmental sensor system (300) that is configured to track patient (302)

throughout healthcare environment (306). Similarly, clinician (304) may be associated with a sensor (310) of environmental sensor system (300) to facilitate tracking of clinician (304) throughout healthcare environment (306). Sensors (308, 310) may be the same or different.

According to an exemplary embodiment, sensor (308) is portable and operatively coupled with (e.g., attached to, affixed to, positioned on, carried by, worn by, etc.) patient (302). Similarly, sensor (310) is portable and operatively coupled with (e.g., attached to, affixed to, positioned on, carried by, worn by, etc.) clinician (304). For example, sensors (308, 310) may be in the form of a tag or other wearable device, similar to those described in U.S. Pat. No. 6,838,992, issued on Jan. 4, 2005, and titled "Methods and Systems For Locating Subjects and Providing Event Notification Within a Tracking Environment and Badge For Use Therein," and U.S. Pat. No. 6,154,139, issued on Apr. 21, 1998, and titled "Method and System For Locating Subjects Within a Tracking Environment," the disclosures of which are incorporated herein by reference.

Figure 4:
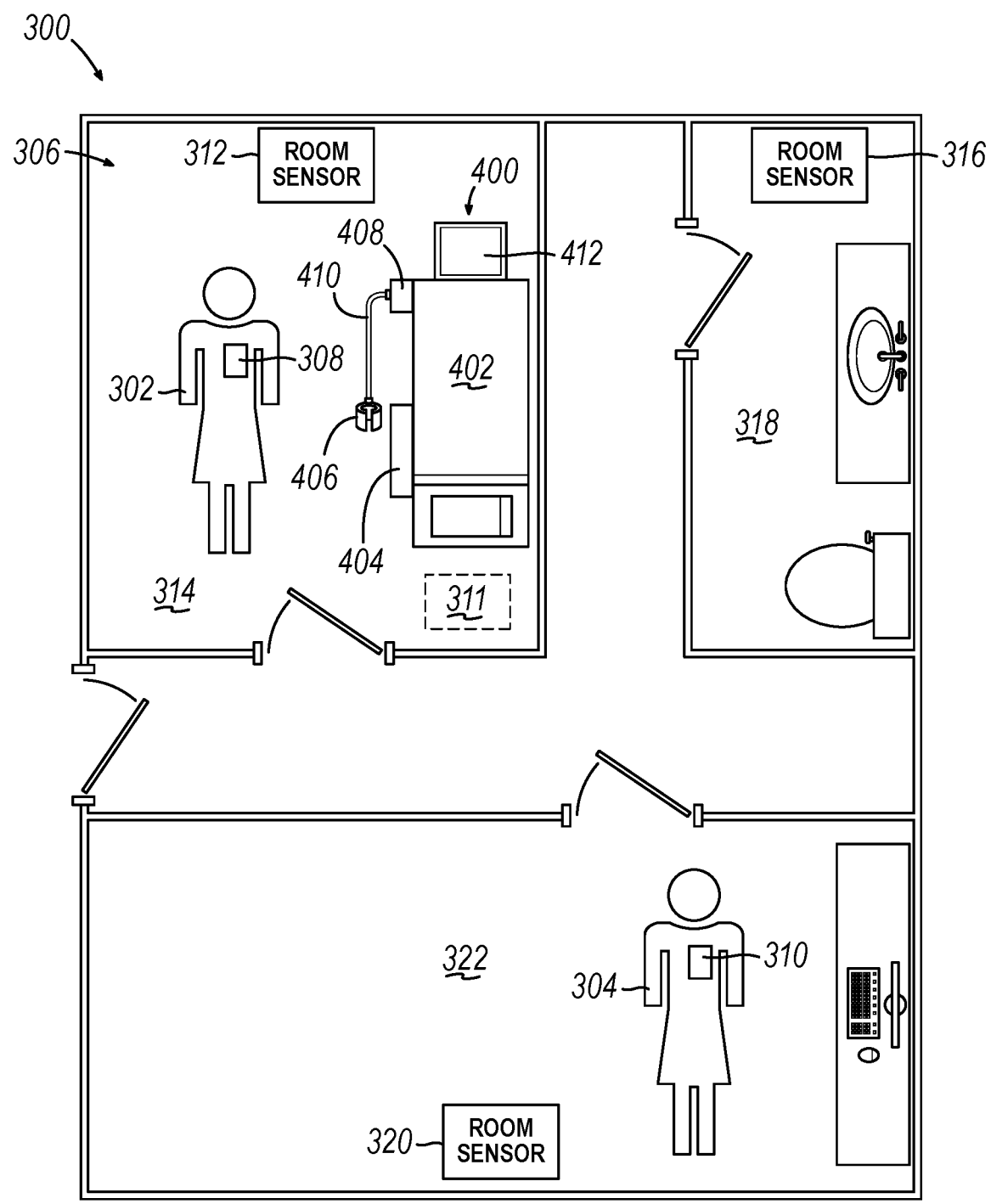
FIG. 4 depicts a diagrammatic view of an exemplary healthcare environment incorporating portions of the patient data collection system of FIG. 1.

In other versions, as shown in phantom in FIG. 4, sensors (308, 310) may be replaced by a biometric or artificial intelligence system (311) configured to recognize individuals moving about healthcare environment (306). A room sensor may be provided and associated with a particular room or particular region in healthcare environment (306) to facilitate the sensing of at least one of patient (302) or clinician (304), as patient (302) and/or clinician (304) moves about healthcare environment (306). The historical movement and time spent in a particular area may be stored in a database similar to database (46).

As shown in FIG. 4, a room sensor (312) may be associated with a first room (e.g., an examination room (314)). Similarly, a room sensor (316) may be associated with a second room (shown as a bathroom (318)). Similarly, a room sensor (320) may be associated with a third room (shown as a processing room (322)). As at least one of patient (302) or clinician (304) moves between examination room (314), bathroom (318), and processing room (322), room sensors (312, 316, 320) receive signals from at least one sensors (308, 310) and collect information (e.g., data) regarding the whereabouts of each individual (e.g., patient (302) or clinician (304)), including the historical movement and the time spent in a particular area or room.

iv. Exemplary Blood Pressure Data Collection System

Figure 5:
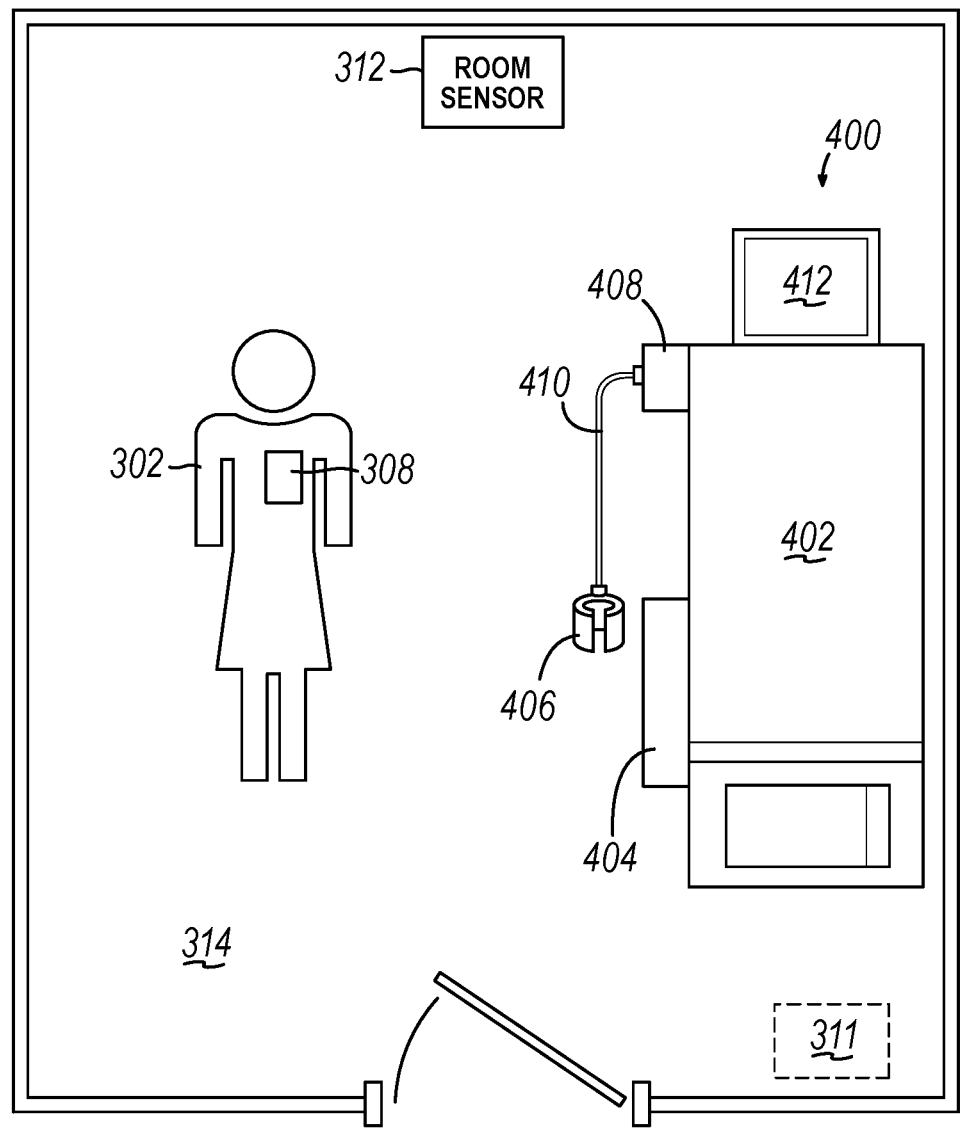
FIG. 5 depicts a diagrammatic view of an exemplary examination room of the healthcare environment of FIG. 4.

As shown in FIGS. 4 and 5, blood pressure data collection system (400) may include an examination table (402), an arm rest (404), a blood pressure collection device (406) such as a blood pressure cuff, a feedback device (408), a data connection (410) between blood pressure collection device (406) and feedback device (408), and a scale (412). For example, one such suitable data collection system is a Digital Vital Signs Device, commercially available from Midmark Corporation, of Dayton, Ohio. For example, one such suitable blood pressure cuff is a Digital Vital Signs Device Reusable Blood Pressure Cuff, commercially available from Midmark Corporation, of Dayton, Ohio. While blood pressure collection device (406) is depicted as connected to examination table (402) through feedback device (408), in other versions of blood pressure collection system (400), blood pressure collection device (406) and/or feedback device (408) may be separate from examination table (402). Blood pressure data collection system (400) is configured to measure the blood pressure of patient (302) and deliver this information to EMR (200) for storage and consideration by clinician (304).

In some versions, blood pressure data collection system (400) is in communication with the environmental sensor system and configured to collect a blood pressure measurement of patient (302) in room (314). In some versions, blood pressure data collection system (400) is configured to initiate the collection of the blood pressure measurement of patient (302) based on the position of either patient (302) or clinician (304), or both. In some versions, blood pressure data collection system (400) is configured to refrain from collecting the blood pressure measurement of patient (302) when clinician (304) is within the room.

Examination table (402) may be used to receive patient (302) thereon and provide a resting place for patient (302) as the blood pressure reading is taken. Some versions of examination table (402) may provide for automatic correction of height to ensure the feet of patient (302) are supported by the floor. The automatic correction may be facilitated by information provided to examination table (402) through the particular medical record (204) assigned to patient (302). More specifically, some versions of examination table (402) may be configured to retrieve the height of patient (302) from the information contained in data field (206c), as shown in FIG. 3, and use this information to automatically adjust the height of examination table (402).

The height of examination table (402) may be adjusted to align the feet of patient (302) flat on the floor, and therefore, in the preferred position for taking blood pressure readings. Alternatively, rather than deriving the correct height of examination table (402) from the height of patient (302), the desired table height of examination table (402) may be directly stored and retrieved from medical record (204). In other versions of examination table (402), examination table (402) automatically raises or lowers in conjunction with continuous measurements obtained through scale (412) to determine when the feet of patient (302) are flat on the floor or in another desirable position such as lifted just off the floor. Logic circuitry is provided for use in determining when the patient is sufficiently lifted, based on the weight measurement provided through scale (412). In other versions of examination table (402), the weight of patient (302) is collected and this information is used to determine when the feet of patient (302) are flat on the floor.

Alternatively, examination table (402) may be configured for manual adjustment of height by patient (302) and/or clinician (304). Examination table (402) may also have a backrest which is movable to abut patient (302) and provide a stable resting area for the torso of patient (302). Examination table (402) may further be configured to store a manual height adjustment within EMR (204) associated with patent (302) for later retrieval and usage on subsequent visits to healthcare environment (306) or usage of examination table (402).

Similar to the adjustment of examination table (402), arm rest (404) may be automatically adjustable or manually adjustable by patient (302) and/or clinician (304). Some versions of arm rest (404) may retrieve biometric data of patient (302) from a particular medical record (204) and adjust the height of arm rest (404) to align with the height of the heart of patient (302). For example, the patient's height may be retrieved from a particular medical record (204) and correlated with a height of the patient's heart, based on the overall height of the patient (e.g. from a lookup table). Alternatively, arm rest (404) may be configured for manual adjustment of height by patient (302) and/or clinician (304). Arm rest (404) may further be configured to store a manual adjustment within EMR (204) associated with patient (302) for later retrieval and usage on subsequent visits to healthcare environment (306) or usage of arm rest (404).

Once patient (302) is sufficiently situated on examination table (402) with an arm optionally resting on arm rest (404) and at heart-height, clinician (304) may apply blood pressure collection device (406) to the arm of patient (302). When applied, blood pressure collection device (406) is capable of measuring the blood pressure of patient (302) and transmitting this information to feedback device (408) through data connection (410). In some versions of patient data collection system (1), blood pressure collection device (406) may be actuated to measure the blood pressure of patient (302) upon actuation of a button or other element by clinician (304). In other versions of patient data collection system (1), blood pressure collection device (406) may be automatically actuated by feedback device (408) to measure the blood pressure of patient (302). In some versions of patient data collection system (1), each available blood pressure collection device (406) includes an identifier, which may be in the form of a Radio-Frequency Identifier (RFID).

Once a particular blood pressure collection device (406) is applied to the patient, the size of the applied blood pressure collection device (406) may be recorded by blood pressure data collection system (400) and stored in the particular medical record (204) associated with patient (302). This data may be useful to provide a recommendation of blood pressure cuff size in the future to a clinician. In other versions of patient data collection system (1), an algorithm may be provided to generate a cuff size recommendation to the clinician based on the height and/or weight of patient (302) stored in medical record (204) associated with patient (302), and a corresponding value in a lookup table.

Feedback device (408) is configured to determine the appropriate time for measuring the blood pressure of patient (302). In some versions of patient data collection system (1), feedback device (408) actuates the measuring of the blood pressure of patient (302) upon the satisfaction of an environment variable such as the expiration of a timer or continuous sensing of the weight of patient (302) on examination table (402) for a set period of time. Waiting to take a blood pressure measurement until after the satisfaction of the environment variable ensures that the patient has sufficient time to relax and become acclimated to the environment, which may lead to a more accurate blood pressure measurement.

As will be discussed in greater detail below, in those versions of patient data collection system (1) where the environmental variable is embodied in a timer, the timer may be initiated in various ways, including via an event sensed by environmental sensor system (300). Upon expiration of the timer, patient data collection system (1) actuates blood pressure data collection system (400) to obtain a blood pressure measurement from a patient disposed in a room of a healthcare facility. In some versions of patient data collection system (1), the event may comprise a clinician associated with the healthcare facility leaving the room. In some versions of patient data collection system (1), the event may comprise a person moving within a healthcare facility. In some versions of patient data collection system (1), the event may comprise the patient moving from a bathroom associated with the healthcare facility into the room. In some versions of patient data collection system (1), the event may comprise the patient moving into a preferred position. The preferred position may be based at least in part on a foot of the patient resting on a floor or resting on a portion of an examination table or any other surface. The preferred position may be based at least in part on an arm of the patient positioned at a particular height. The preferred position may be based in part on a heartrate and/or a preferred sitting or resting position. The timer may also be terminated when environmental sensor system (300) senses an interruption. In some versions of patient data collection system (1), the interruption may comprise the clinician or another person entering the room. The blood pressure measurement is not obtained from the patient when the timer is terminated.

The timer may be started when clinician (304) leaves examination room (314). This information may be provided by clinician (304) actuating a button, a door sensor, or provided through room sensor (312) sensing that clinician (304) has moved out of range via signals between room sensor (312) and sensor (310). Upon manually or automatically sensing clinician (304) has left examination room (314), environmental sensor system (300) signals to feedback device (408) the occurrence of this event, which in turn, may actuate feedback device (408) to begin the timer. Upon expiration of the timer, feedback device (408), by way of data connection (410), may actuate blood pressure collection device (406) to measure the blood pressure of patient (302).

The timer may alternatively be associated with scale (412) and initiated by the sensing of the weight of patient (302) by scale (412). For example, upon patient (302) resting on scale (412), feedback device (408) may begin the timer based on scale (412) reading a greater than zero weight measurement. To ensure patient (302) continues to rest on examination table (402), feedback device (408) may continuously poll scale (412) to determine whether patient (302) has remained on examination table (402) for a set period of time. Alternatively, scale (412) may proactively send a signal to feedback device (408) upon any dramatic decrease in the weight on scale (412), which may represent patient (302) moving off examination table (402). The weight sensing of scale (412) may be alternatively initiated by sensing of clinician (304) leaving examination room (314), provided through environmental sensor system (300). Upon the clinician leaving examination room (314), feedback device (408) and scale (412) may begin sensing the weight on scale (412) to determine whether patient (302) is sitting on examination table (402) and start the timer.

Once the timer expires, feedback device (408) may actuate blood pressure collection device (406) to initiate measuring the blood pressure of patient (302). After the blood pressure of patient (302) is measured and passed to feedback device (408) via data connection (410), feedback device (408) provides the measurement data to EMR system (200) for storage in the particular medical record (204) associated with patient (302).

After the blood pressure of patient (302) is measured and stored in EMR system (200), clinician (304) may be notified either directly or indirectly. For example, clinician (304) may be directly notified by way of sensor (310), using any one or more of vibration, an audible signal, a visual signal, or environmental sensor system (300). Similarly, a feedback mechanism or display within processing room (322) may be actuated to indirectly alert clinician (304) that the blood pressure of patient (302) has been measured and stored in EMR system (200). For example, feedback device (408) may signal a computer or other electronic device within processing room (322) or otherwise associated with clinician (304) or healthcare environment (306) to update a status associated with patient (302) to reflect the blood pressure has been measured. Once blood pressure of patient (302) is measured and stored, and clinician (304) may be notified and clinician (304) may attend to patient (302) accordingly.

Figure 6:
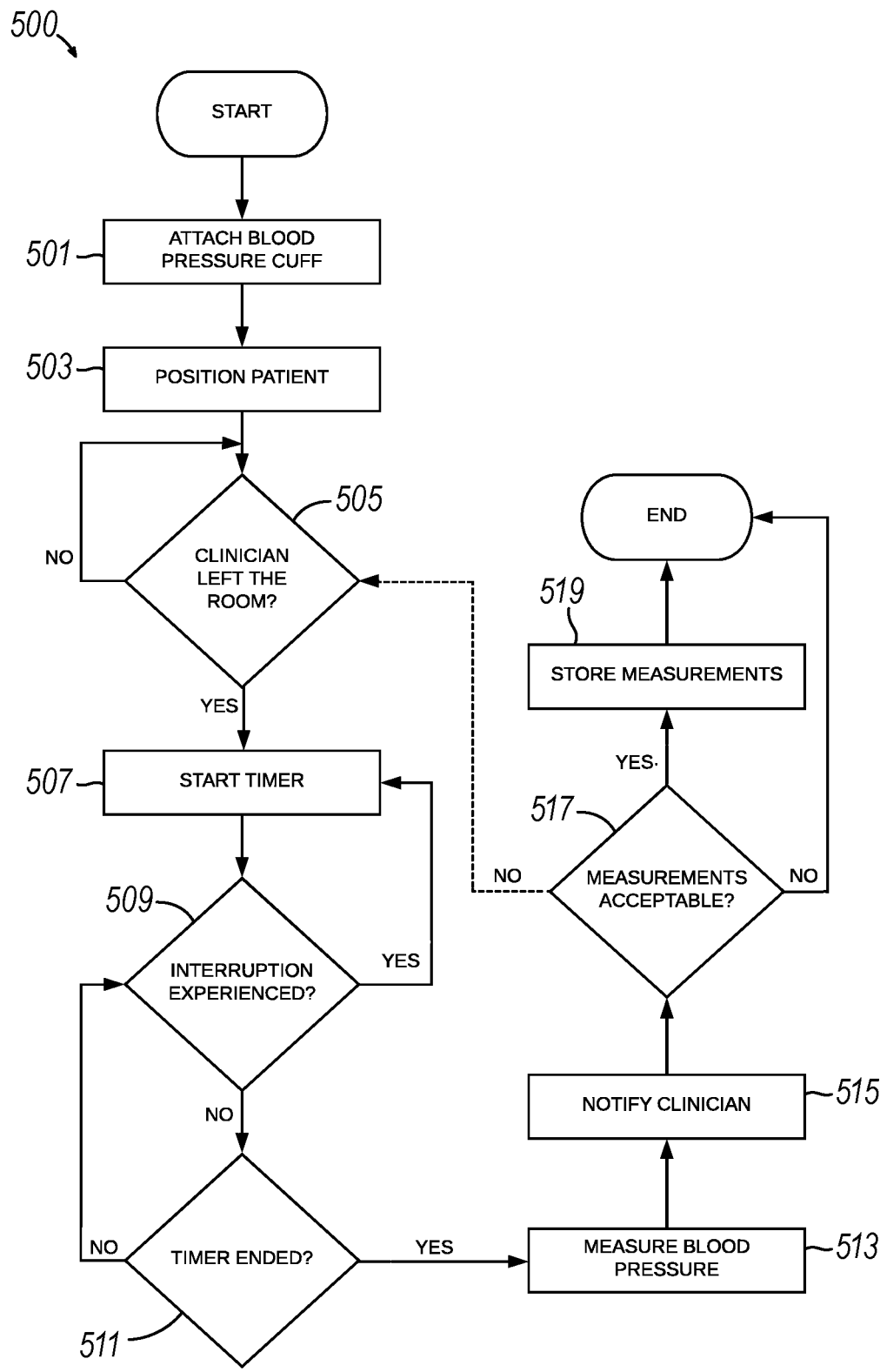
FIG. 6 depicts a flowchart of an exemplary method for collecting patient data.

II. EXEMPLARY PATIENT DATA COLLECTION METHODS i. First Patient Data Collection Methods Various methods may be used within patient data collection system (1) for collecting a patient's blood pressure within a healthcare environment. For example, as shown in FIG. 6, a patient data collection method (500) may begin with a step (501). In step (501), a clinician or other healthcare worker attaches a blood pressure cuff to a patient's arm, with the patient residing in an examination room. Thereafter, step (501) proceeds to a step (503), whereby environmental adjustments are made regarding the examination room and/or the patient's posture, seating arrangement, or proper positioning. For example, if the patient is resting on an examination table, the height of the examination table may be adjusted to ensure the patient's feet are resting flat on a surface (e.g., the ground or a foot rest). In some other versions of step (503), the height of the examination table may be adjusted to ensure the patient's feet are lifted off of the ground entirely. In some versions of step (503), the height or placement of an arm rest associated with the examination table may be adjusted to align the patient's arm with the patient's heart, or any other desired placement or orientation of the patient's arm.

In some versions of step (503), the examination table and/or the arm rest adjustment is performed automatically. This automatic adjustment may be based on patient data retrieved from an electronic medical records system similar to medical record (204a) depicted in FIG. 3. For example, the patient's height and weight and/or preferred table height may be retrieved from an electronic medical records system and used by intelligence logic associated with the examination table to adjust the table a desired height, based on the patient's height and weight data. In other versions of step (503), the back rest of the examination table is adjusted to the patient, either automatically or manually, and may be based on information retrieved from an electronic medical records system. In some versions of step (503), all the environmental adjustments and/or patient positioning changes are performed at the same general time. For example, the arm support may be raised to approximately the patient's heart height while the back rest is simultaneously moved to properly position the patient.

In some versions of step (503), after the patient is properly positioned, the patient's weight may be captured using load cells disposed in the examination table. The captured weight data is thereafter transmitted and stored in the electronic medical record associated with that patient. The examination table and/or load cells may be configured to sense when a patient's feet are on and off the floor and automatically adjust the examination table to a desired height for the patient when the patient's feet are determined to be flat on the floor.

As shown in FIG. 6, after sufficient environmental adjustments are performed, step (503) proceeds to a step (505), whereby it is determined whether the clinician has left the examination room. This determination may be performed automatically by way of sensors associated with the clinician and/or the examination room. For example, the clinician may be wearing a sensor tag for providing signals to a room sensor, such as electromagnetic signals provided by an electromagnetic device, ultrasonic signals provided by an ultrasonic device, or other signals provided by other suitable devices. More specifically, it may be determined that the clinician has left the examination room when the room sensor detects an absence of the signals emanating from the clinician's sensor tag. Step (505) may repeat until it is determined the clinician has left the examination room, and thereafter, step (505) proceeds to a step (507). In step (507), a timer is initiated for a set amount of time via timer circuitry. The length of the timer may be configured by a user or otherwise set or adjusted. Alternatively, the length of the timer may be static and non-adjustable.

During the timer, or during any other part of patient data collection method (500), environmental adjustments such as soothing music or white noise may be introduced into examination room (314) to help relax the patient. For example, bird or beach sounds may be played for the patient. The sounds may be generated through blood pressure collection device (406) or feedback device (408) or any other elements of blood pressure data collection system (400) such as a speaker. The sounds may be intended to relax the patient, which may result in a more accurate collection of patient data.

In some versions of patient data collection method (500), after the timer is started, step (507) proceeds to a step (509), whereby it is determined whether at least one of the patient or the environment has been interrupted. According to an exemplary embodiment, the patient has been interrupted if the patient stands up from the examination table, the patient falls from the examination table, and/or the blood pressure data collection system (400) picks up a noticeable movement of the patient (e.g., using sensor (308) or room sensor (312)). According to an exemplary embodiment, the environment has been interrupted if a healthcare provider enters the room or a sound or other distraction occurs in the room (e.g., using sensor (310) or room sensor (312)). If at least one of the patient or environment has been interrupted in step (509), method (500) proceeds back to step (507) and the timer restarts. In other versions of patient data collection method (500), if the patient and/or environment has been interrupted, step (509) automatically notifies the clinician and the clinician may reenter the room to address the interruption and restart the process. The determination of whether the patient and/or the environment has been interrupted may be based on data provided through the sensors on the patient or healthcare provider, or by sensors in the examination room, or by the load cells or other weight sensing features of the examination table. If step (509) determines that the patient and the environment has not been interrupted, step (509) proceeds to a step (511), whereby it is determined whether the timer has ended or lapsed. Step (511) loops back to step (509) until it is determined the timer has lapsed. Once the timer has lapsed, step (511) transitions to a step (513). In some versions of patient data collection method (500), step (509) is omitted, and step (507) proceeds directly to step (511), whereby step (511) loops back upon itself until it is determined the timer has ended.

In step (513), the patient's blood pressure is measured by way of the blood pressure cuff attached to the patient in step (501). Upon initiation of step (513), the patient has been sitting in a relaxed manner for the duration of the timer and preferably out of sight of the clinician. Therefore, the blood pressure measurement obtained in step (513) is taken in a controlled and calm environment and after a period of time to allow the patient to relax in furtherance of taking an accurate blood pressure measurement. The potentially stressful environmental factors prior to the blood pressure measurement such as walking to or moving around in the examination room, interacting with a clinician, or any other undesired factor, are minimized by having the patient wait for a set amount of time prior to the blood pressure measurement.

After step (513), patient data collection method (500) moves to a step (515). In step (515), the clinician is notified that the patient's blood pressure has been measured. This notification may be facilitated by a notification on a computer screen or status board, actuating the clinician's sensor or another personal electronic device, or by any other mechanism for alerting the clinician the patient's blood pressure has been measured and collected. Once the clinician has been notified that the patient's blood pressure has been measured, step (515) proceeds to a step (517).

In step (517), the healthcare provider such as the physician or clinician reviews the measurements and determined whether the measurements are acceptable. If the measurements are generally in line with what is expected from the patient, the healthcare provider then approves of the measurements and step (517) proceeds to a step (519). If the measurements are not acceptable, the clinician declines the measurements. As shown in FIG. 6, in some versions of patient data collection method (500), after the clinician declines the measurements, patient data collection method (500) proceeds to end. In other versions of patient data collection method (500), after the clinician declines to accept the measurements, step (517) proceeds back to step (505) to repeat the measurement collection process, as shown in the dashed line. Measurement results may be accepted or declined by the clinician by any mechanism, including actuation of a physical button or by selecting the preferred action on a touchscreen or any other input mechanism. As shown in FIG. 6, upon acceptance of the blood pressure measurements by the clinician, step (515) proceeds to a step (519). While not shown, it is also envisioned that blood pressure data collection system (400) may automatically determine whether the blood pressure measurements are within an acceptable range.

In step (519), the blood pressure measurements are stored for further use by the clinician or healthcare facility. For example, the blood pressure measurements may be transmitted, either through wires or wirelessly, to an electronic medical records system for storage. Once the blood pressure measurements are stored in step (519), patient data collection method (500) terminates. It is also envisioned that the blood pressure measurements may be manually recorded into the electronic medical records system or into a physical medical records system.

In other versions of method (500), after the clinician leaves the examination room, blood pressure measurements of the patient may be taken immediately. After this initial blood pressure measurement is taken, method (500) may wait for a set amount of time and retake the blood pressure measurement. This may be repeated as many times as desired or configured within the blood pressure data collection system. The collected blood pressure data points may thereafter be averaged together or otherwise combined to provide a final measurement. For example, the first collected blood pressure reading for the patient may be discarded and used simply to get the patient used to the blood pressure collection methodologies. As such, it is also envisioned that method (500) may include multiple blood pressure data points, which may be averaged to otherwise combined to provide a final measurement Successive blood pressure readings may be more accurate in that the patient is not experiencing the collection method for the first time and may be in a more relaxed and natural state of rest. Variables such as the wait time in between each blood pressure collection, number of measurements, or which measurements to use may be configured by a user of the system, such as a particular clinician or may be set by the administrators of the healthcare environment.

In other versions of method (500), method (500) may be configured to measure the pulse rate of the patient. The pulse rate of the patient may be obtained by partially inflating the blood pressure cuff In some versions, the pulse rate may be monitored and when method (500) determines the patient's pulse rate has leveled out to a calm resting pulse, blood pressure readings may be taken from the patient. In other versions, the pulse rate may be measured while steps (507, 508, 509) are proceeding and the system is waiting for the timer to end. In either configuration, the raw pulse data may be fed into the electronic medical record associated with the patient for record keeping and updating of the vital statistic.

In other versions of method (500) a digital checklist may be provided on a computer screen, graphical display or other I/O device associated with the examination room. The checklist is configured to guide the clinician through many of the steps associated with method (500). The checklist may be provided via software connected with the electronical medical record system and may prompt the clinician to acquire or collect various data points for insertion into the medical record associated with the patient. For example, the checklist may include a first entry related to collecting the weight of the patient or to actuate a digital button to initiate the blood pressure collection process. This checklist reminds and prompts the clinician of the steps involved in receiving a patient into the examination room, rather than initiating some of the steps through actuation by the scale of the examination table or similar automatic processes. In these versions of method (500), the checklist prompts the clinician to manually actuate the steps.

ii. Second Patient Data Collection Method

Figure 7:
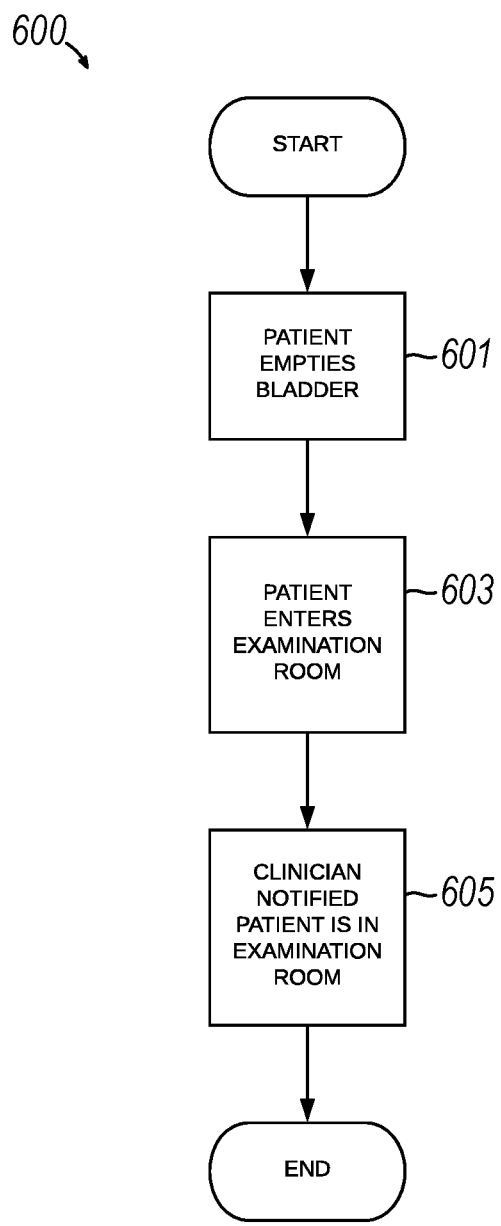
FIG. 7 depicts a flowchart of another exemplary method for collecting patient data.

As shown in FIG. 7, a patient data collection method (600) may be used within patient data collection system (1) for collecting a patient's blood pressure within a healthcare environment. Patient data collection method (600) may be incorporated into portions of patient data collection method (500) or may be used independently from patient data collection method (500). Patient data collection method (600) may begin with a step (601), whereby a patient uses a restroom and to empty the patient's bladder. This step may be aided by providing directions to the restroom via a wearable tag or other personal electronic device provided to the patient. Further, the use of the restroom may be monitored by way of a sensor tag worn or carried by the user and a corresponding room sensor provided in the bathroom. FIG. 4 provides an example embodiment of this interaction through sensor (308) and bathroom (318) having room sensor (316) disposed therein. As the patient enters and leaves bathroom (318), sensor (308) interacts with room sensor (316) to determine the patient spent time within bathroom (318). Thereafter step (601) moves to a step (603).

In step (603), the patient moves from the restroom to the examination room. This step may be aided by providing directions from the restroom to the examination room via a wearable tag or other personal electronic device provided to the patient. The patient's entering of the examination room may be monitored by way of a sensor tag worn or carried by the user and corresponding to a room sensor provided in the examination room. For example, as illustrated in FIGS. 4 and 5, sensor (308) may interact with room sensor (312) to determine when the patient enters examination room. Upon entry of the patient into the examination room, step (603) moves to a step (605).

In step (605), the clinician is notified the patient is within the examination room. As discussed in more detail above, the notification process may involve an indication on a computer screen or other display associated with the clinician or any other visual or audible indicator. Alternatively, a wearable tag or other personal electronic device associated with the clinician may be used to indicate the patient is within the examination room. The notification may be actuated by the examination table sensing a weight thereon as the patient sits down onto the examination table. This increase in weight, as sensed by the scale of the examination table, triggers or actuates a mechanism for indicating to the clinician that the patient is within the examination room. Once the clinician is notified the patient is within the examination room, patient data collection method (600) terminates.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of collecting patient data, the method comprising: (a) starting a timer; and (b) upon expiration of the timer, actuating a blood pressure data collection system to obtain a blood pressure measurement from a patient disposed in a room of a healthcare facility.

Example 2

The disclosure of the previous Example or any of the subsequent Examples, further comprising: (a) sensing an event with an environmental sensor system associated with the healthcare facility; and (b) in response to sensing the event, starting the timer.

Example 3

The disclosure of any of the previous or subsequent Examples, wherein the event comprises a clinician associated with the healthcare facility leaving the room.

Example 4

The disclosure of any of the previous or subsequent Examples, further comprising: (a) sensing an interruption with the environmental sensor system; and (b) in response to sensing the interruption, terminating the timer.

Example 5

The disclosure of any of the previous or subsequent Examples, wherein the interruption comprises a person entering the room.

Example 6

The disclosure of any of the previous or subsequent Examples, wherein the event comprises a person moving within a healthcare facility.

Example 7

The disclosure of any of the previous or subsequent Examples, wherein the event comprises the patient moving into a preferred position.

Example 8

The disclosure of any of the previous or subsequent Examples, wherein the preferred position is based at least in part on a foot of the patient resting on a floor.

Example 9

The disclosure of any of the previous or subsequent Examples, wherein the preferred position is based at least in part on an arm of the patient positioned at a particular height.

Example 10

The disclosure of any of the previous or subsequent Examples, wherein the event comprises the patient moving from a bathroom associated with the healthcare facility into the room.

Example 11

The disclosure of any of the previous or subsequent Examples, wherein the event comprises placement of a blood pressure cuff associated with the blood pressure data collection system on the patient.

Example 12

The disclosure of any of the previous or subsequent Examples, further comprising, in response to obtaining the blood pressure measurement of the patient, notifying a clinician associated with the healthcare facility and not in the room the blood pressure measurement has been obtained.

Example 13

The disclosure of any of the previous or subsequent Examples, further comprising: (a) providing the blood pressure measurement to the clinician; and (b) prompting the clinician to accept or reject the blood pressure measurement.

Example 14

The disclosure of any of the previous or subsequent Examples, further comprising, in response to the clinician rejecting the blood pressure measurement: (a) starting the timer; and (b) upon expiration of the timer, actuating the blood pressure data collection system to obtain a second blood pressure measurement from the patient.

Example 15

The disclosure of any of the previous or subsequent Examples, further comprising, in response to the clinician accepting the blood pressure measurement, storing the blood pressure measurement in an electronic medical record associated with the patient.

Example 16

A method of collecting patient data, the method comprising: (a) starting a timer; and (b) upon expiration of the timer, electronically actuating a blood pressure cuff connected to a patient disposed in a room of a healthcare facility to obtain a blood pressure measurement of the patient.

Example 17

The disclosure of any of the previous or subsequent Examples, further comprising: (a) sensing a clinician associated with the healthcare facility leaving the room; and (b) in response to sensing the clinician leaving the room, starting the timer.

Example 18

The disclosure of any of the previous or subsequent Examples, further comprising: (a) sensing the clinician entering the room; and (b) in response to sensing the clinician entering the room, terminating the timer.

Example 19

The disclosure of any of the previous or subsequent Examples, further comprising preventing the blood pressure cuff from obtaining a blood pressure measurement of the patient while the clinician is within the room.

Example 20

A method of collecting patient data, the method comprising: (a) sensing an event within a healthcare facility via an environmental sensor system associated with the healthcare facility, wherein the event is based at least in part on movement of a person within the healthcare facility; (b) based on sensing the event, starting a timer; (c) upon expiration of the timer, actuating a blood pressure data collection system to obtain a blood pressure measurement of a patient disposed in a room of the healthcare facility.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of collecting patient data, the method comprising:
    (a) sensing an event within a healthcare facility via an environmental sensor system associated with the healthcare facility, wherein the event is based at least in part on movement of a person within the healthcare facility;
    (b) based on sensing the event, automatically starting a timer; and
    (c) upon expiration of the timer, automatically actuating a blood pressure data collection system to obtain blood pressure measurement of a patient disposed in a room of the healthcare facility.

2. The method of claim 1, wherein the event comprises a clinician associated with the healthcare facility leaving the room.

3. The method of claim 1, further comprising:
    (a) sensing an interruption with the environmental sensor system; and
    (b) in response to sensing the interruption, terminating the timer.

4. The method of claim 3, wherein the interruption comprises a person entering the room.

5. The method of claim 1, wherein the event comprises the patient moving from a bathroom associated with the healthcare facility into the room.

6. The method of claim 1, further comprising, in response to obtaining the blood pressure measurement of the patient, notifying a clinician associated with the healthcare facility and not in the room the blood pressure measurement has been obtained.

7. The method of claim 6, further comprising:
   (a) providing the blood pressure measurement to the clinician; and
   (b) prompting the clinician to accept or reject the blood pressure measurement.

8. The method of claim 7, further comprising, in response to the clinician rejecting the blood pressure measurement:
   (a) starting the timer; and
   (b) upon expiration of the timer, actuating the blood pressure data collection system to obtain a second blood pressure measurement from the patient.

9. The method of claim 7, further comprising, in response to the clinician accepting the blood pressure measurement, storing the blood pressure measurement in an electronic medical record associated with the patient.

\* \* \* \* \*